US010105644B2

(12) United States Patent
Zehnacker et al.

(10) Patent No.: US 10,105,644 B2
(45) Date of Patent: Oct. 23, 2018

(54) PROCESS AND ABSORBENT FOR DEHUMIDIFYING MOIST GAS MIXTURES (71) Applicant: Evonik Degussa GmbH, Essen (DE)

(72) Inventors: Olivier Zehnacker, Dortmund (DE); Benjamin Willy, Düsseldorf (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/619,584

(22) Filed: Jun. 12, 2017

(65) Prior Publication Data
US 2017/0354922 A1    Dec. 14, 2017

(30) Foreign Application Priority Data

Jun. 14, 2016   (DE) .................. 10 2016 210 483

(51) Int. Cl.
| B01D 53/26 | (2006.01) |
| B01D 53/77 | (2006.01) |
| B01D 53/78 | (2006.01) |
| C07C 9/02 | (2006.01) |
| C07D 233/56 | (2006.01) |
| C07F 9/09 | (2006.01) |
| C07F 9/11 | (2006.01) |
| C01D 5/00 | (2006.01) |

(52) U.S. Cl.
CPC ......... *B01D 53/263* (2013.01); *C07D 233/56* (2013.01); *C07F 9/091* (2013.01); *C07F 9/11* (2013.01); *B01D 2251/61* (2013.01); *B01D 2252/20473* (2013.01); *C01D 5/00* (2013.01)

(58) Field of Classification Search
CPC .... B01D 53/263; B01D 53/26; B01D 53/261; B01D 53/77; B01D 53/78; C07F 9/11; C07F 9/091; C07F 9/02; C07D 233/56
See application file for complete search history.

(56) References Cited

U.S. PATENT DOCUMENTS

| 1,882,258 A | 10/1932 | Randel |
| 2,516,625 A | 7/1950 | Haury |
| (Continued) | | |

FOREIGN PATENT DOCUMENTS

| CA | 2 817 704 | 5/2012 |
| CN | 1076380 A | 9/1993 |
| (Continued) | | |

OTHER PUBLICATIONS

Kanakubo, et al., "$CO_2$ solubility in and physical properties for ionic liquid mixtures of 1-butyl-3-methylimidazolium acetate and 1-butyl-3-methylimidazolium bis(trifluoromethanesulfonyl)amide," *Journal of Molecular Liquids* 217:112-119 (2016); available online Feb. 12, 2016.

(Continued)

*Primary Examiner* — Timothy C Vanoy
(74) *Attorney, Agent, or Firm* — Law Office of: Michael A. Sanzo, LLC (57) ABSTRACT The invention relates to a process for dehumidifying a moist gas mixture in which the moist gas mixtures are brought into contact with an absorbent comprising dialkylimidazolium salts and trialkyl phosphate. In addition, the invention also relates to an absorption heat pump comprising the absorbent according to the invention and to the absorbent according to the invention itself.

20 Claims, 2 Drawing Sheets

(56) References Cited

U.S. PATENT DOCUMENTS

| | | | |
|---|---|---|---|
| 2,601,673 A | 6/1952 | McMillan et al. |
| 2,802,344 A | 8/1957 | Witherell |
| 3,276,217 A | 10/1966 | Bourne et al. |
| 3,317,654 A | 5/1967 | Yonkers |
| 3,580,759 A | 5/1971 | Albertson et al. |
| 3,609,087 A | 9/1971 | Chi et al. |
| 3,927,151 A * | 12/1975 | Ismail ................ C07F 9/02 |
| | | | 558/100 |
| 4,046,719 A * | 9/1977 | Stanaback ............. C07F 9/091 |
| | | | 106/170.15 |
| 4,079,263 A | 3/1978 | Inoue |
| 4,094,957 A | 6/1978 | Sartori et al. |
| 4,106,904 A | 8/1978 | Oude Alink et al. |
| 4,112,051 A | 9/1978 | Sartori et al. |
| 4,152,900 A | 5/1979 | Chopra et al. |
| 4,152,901 A | 5/1979 | Munters |
| 4,201,721 A | 5/1980 | Hallgren |
| 4,217,238 A | 8/1980 | Satori et al. |
| 4,251,494 A | 2/1981 | Say |
| 4,360,363 A | 11/1982 | Ferrin et al. |
| 4,405,579 A | 9/1983 | Sartori et al. |
| 4,405,586 A | 9/1983 | Sartori et al. |
| 4,466,915 A | 8/1984 | Lai |
| 4,489,563 A | 12/1984 | Kalina |
| 4,524,587 A | 6/1985 | Kantor |
| 4,525,294 A | 6/1985 | Sartori et al. |
| 4,605,743 A | 8/1986 | Malz et al. |
| 4,643,000 A | 2/1987 | Rheinfelder |
| 4,701,530 A | 10/1987 | Swearingen et al. |
| 4,714,597 A | 12/1987 | Trevino |
| 4,889,938 A | 12/1989 | Kristen et al. |
| 5,016,445 A | 5/1991 | Wehr |
| 5,126,189 A | 6/1992 | Tanny et al. |
| 5,186,009 A | 2/1993 | Rockenfeller |
| 5,186,010 A | 2/1993 | Wehr |
| 5,245,070 A * | 9/1993 | Nishikawa .......... B01F 17/0064 |
| | | | 106/2 |
| 5,255,534 A | 10/1993 | Ryan |
| 5,303,565 A | 4/1994 | Pravada |
| 5,390,509 A | 2/1995 | Rockenfeller et al. |
| 5,583,270 A | 12/1996 | Nishiguchi |
| 5,873,260 A | 2/1999 | Linhardt et al. |
| 6,117,963 A | 9/2000 | Boinowitz et al. |
| 6,128,917 A | 10/2000 | Riesch et al. |
| 6,130,347 A | 10/2000 | Julius et al. |
| 6,155,057 A | 12/2000 | Angell et al. |
| 6,165,433 A | 12/2000 | Chakravarti et al. |
| 6,184,433 B1 | 2/2001 | Harada et al. |
| 6,423,282 B1 | 7/2002 | Araki et al. |
| 6,475,370 B2 | 11/2002 | Lehmann et al. |
| 6,672,099 B1 | 1/2004 | Yoshimi et al. |
| 6,680,047 B2 | 1/2004 | Klaveness et al. |
| 6,727,015 B1 | 4/2004 | Putter et al. |
| 7,419,646 B2 | 9/2008 | Cadours et al. |
| 7,435,318 B2 | 10/2008 | Arlt et al. |
| 7,638,636 B2 | 12/2009 | Zhou et al. |
| 7,666,813 B2 | 2/2010 | Hoefer et al. |
| 7,754,053 B2 | 7/2010 | Maase |
| 7,827,820 B2 | 11/2010 | Weimer et al. |
| 7,998,714 B2 | 8/2011 | Gellett et al. |
| 8,069,687 B2 | 12/2011 | Jork et al. |
| 8,167,983 B2 | 5/2012 | Seiler et al. |
| 8,277,615 B2 | 10/2012 | Ruffert et al. |
| 8,318,117 B2 | 11/2012 | Lichtfers et al. |
| 8,357,344 B2 | 1/2013 | Bouillon et al. |
| 8,362,095 B2 | 1/2013 | Schwab et al. |
| 8,382,962 B2 | 2/2013 | Massonne et al. |
| 8,470,079 B2 | 6/2013 | Agar et al. |
| 8,500,867 B2 | 8/2013 | Seiler et al. |
| 8,500,892 B2 | 8/2013 | Seiler et al. |
| 8,506,839 B2 | 8/2013 | Shiflett et al. |
| 8,523,978 B2 | 9/2013 | Rojey et al. |
| 8,623,123 B2 | 1/2014 | Seiler et al. |
| 8,696,928 B2 | 4/2014 | Seiler et al. |
| 8,703,451 B2 | 4/2014 | Haas et al. |
| 8,715,521 B2 | 5/2014 | Shiflett et al. |
| 8,784,537 B2 | 7/2014 | Seiler et al. |
| 8,809,576 B2 | 8/2014 | Schraven et al. |
| 8,932,478 B2 | 1/2015 | Seiler et al. |
| 9,221,007 B2 | 12/2015 | Rolker et al. |
| 9,409,122 B2 | 8/2016 | Qi et al. |
| 9,630,140 B2 | 4/2017 | Willy et al. |
| 9,840,473 B1 | 12/2017 | Wang et al. |
| 9,878,285 B2 | 1/2018 | Schraven et al. |
| 2004/0016631 A1 | 1/2004 | Madkour |
| 2004/0133058 A1 | 7/2004 | Arlt et al. |
| 2005/0070717 A1 | 3/2005 | Wasserscheid et al. |
| 2005/0129598 A1 | 6/2005 | Chinn |
| 2005/0164082 A1 | 7/2005 | Kishi et al. |
| 2005/0202967 A1 | 9/2005 | Hoefer et al. |
| 2005/0245769 A1 | 11/2005 | Kohler et al. |
| 2006/0104877 A1 | 5/2006 | Cadours et al. |
| 2006/0150665 A1 | 7/2006 | Weimer et al. |
| 2006/0197053 A1 | 9/2006 | Shiflett et al. |
| 2006/0251961 A1 | 11/2006 | Olbert et al. |
| 2006/0264645 A1 | 11/2006 | Zhou et al. |
| 2007/0004903 A1 | 1/2007 | Hoff et al. |
| 2007/0095645 A1 | 5/2007 | Masse |
| 2007/0144186 A1 | 6/2007 | Shiflett et al. |
| 2007/0164462 A1 | 7/2007 | Liu et al. |
| 2007/0264180 A1 | 11/2007 | Carrette et al. |
| 2007/0286783 A1 | 12/2007 | Carrette et al. |
| 2008/0028777 A1 | 2/2008 | Boesmann et al. |
| 2008/0114105 A1 | 5/2008 | Hell et al. |
| 2008/0283383 A1 | 11/2008 | Ruffert et al. |
| 2009/0029121 A1 | 1/2009 | Hammermann et al. |
| 2009/0029887 A1 | 1/2009 | Schwab et al. |
| 2009/0036334 A1 | 2/2009 | Schwab et al. |
| 2009/0139232 A1 | 6/2009 | Collis |
| 2009/0170734 A1 | 7/2009 | Schwab et al. |
| 2009/0199709 A1 | 8/2009 | Rojey et al. |
| 2009/0211447 A1 | 8/2009 | Lichtfers et al. |
| 2010/0011958 A1 | 1/2010 | Cadours et al. |
| 2010/0016205 A1 | 1/2010 | Schwab |
| 2010/0029519 A1 | 2/2010 | Schwab et al. |
| 2010/0071557 A1 | 3/2010 | Seiler et al. |
| 2010/0084597 A1 | 4/2010 | Schwab et al. |
| 2010/0086983 A1 | 4/2010 | Gellett et al. |
| 2010/0095703 A1 | 4/2010 | Jork et al. |
| 2010/0104490 A1 | 4/2010 | Bouillon et al. |
| 2010/0132551 A1 | 6/2010 | Bouillon et al. |
| 2010/0186590 A1 | 7/2010 | Vorberg et al. |
| 2010/0192770 A1 | 8/2010 | Andarcia |
| 2010/0269528 A1 | 10/2010 | Gerhard et al. |
| 2010/0288126 A1 | 11/2010 | Agar et al. |
| 2010/0300870 A1 | 12/2010 | Massonne et al. |
| 2010/0326126 A1 | 12/2010 | Seiler et al. |
| 2011/0000236 A1 | 1/2011 | Seiler et al. |
| 2011/0081287 A1 | 4/2011 | Bouillon et al. |
| 2011/0094381 A1 | 4/2011 | Lichtfers et al. |
| 2011/0118504 A1 | 5/2011 | Haas et al. |
| 2011/0135549 A1 | 6/2011 | Lichtfers et al. |
| 2011/0185901 A1 | 8/2011 | Jacquin et al. |
| 2011/0247494 A1 | 10/2011 | Dinnage et al. |
| 2011/0256043 A1 | 10/2011 | Blair et al. |
| 2011/0309295 A1 | 12/2011 | Joh et al. |
| 2012/0011886 A1 | 1/2012 | Shiflett et al. |
| 2012/0017762 A1 | 1/2012 | Seiler et al. |
| 2012/0024756 A1 | 2/2012 | Verma et al. |
| 2012/0080644 A1 | 4/2012 | Seiler et al. |
| 2012/0117991 A1 | 5/2012 | Rached |
| 2012/0186993 A1 | 7/2012 | Huang et al. |
| 2012/0247144 A1 | 10/2012 | Seiler et al. |
| 2012/0308458 A1 | 12/2012 | Seiler et al. |
| 2012/0315366 A1 | 12/2012 | Zehnacher et al. |
| 2013/0011314 A1 | 1/2013 | Porcheron et al. |
| 2013/0023712 A1 | 1/2013 | Porcheron et al. |
| 2013/0031930 A1 | 2/2013 | Seiler et al. |
| 2013/0031931 A1 | 2/2013 | Seiler et al. |
| 2013/0118350 A1 | 5/2013 | Rolker et al. |
| 2013/0133327 A1 | 5/2013 | Milam et al. |
| 2013/0219949 A1 | 8/2013 | Seiler et al. |
| 2013/0247758 A1 | 9/2013 | Seiler et al. |
| 2013/0255496 A1 | 10/2013 | Zhang et al. |

(56) References Cited

U.S. PATENT DOCUMENTS

| | | |
|---|---|---|
| 2013/0263743 A1 | 10/2013 | Seiler et al. |
| 2013/0319022 A1 | 12/2013 | Becze et al. |
| 2013/0327084 A1 | 12/2013 | Shiflett et al. |
| 2014/0005344 A1 | 1/2014 | Rinker et al. |
| 2014/0090558 A1 | 4/2014 | Rolker et al. |
| 2014/0105801 A1 | 4/2014 | Rolker et al. |
| 2014/0120016 A1 | 5/2014 | Rolker et al. |
| 2014/0127103 A1 | 5/2014 | Qi et al. |
| 2014/0356268 A1 | 12/2014 | Schraven et al. |
| 2014/0360369 A1 | 12/2014 | Schraven et al. |
| 2015/0024106 A1 | 1/2015 | Huller et al. |
| 2015/0024247 A1 | 1/2015 | Lockett et al. |
| 2015/0125373 A1 | 5/2015 | Willy et al. |
| 2015/0175738 A1 | 6/2015 | Willy et al. |
| 2015/0175740 A1 | 6/2015 | Willy et al. |
| 2015/0308720 A1 | 10/2015 | Zehnacker et al. |
| 2015/0321139 A1 | 11/2015 | Schraven et al. |
| 2016/0045857 A1 | 2/2016 | Rolker et al. |
| 2016/0115827 A1 | 4/2016 | Rached |
| 2016/0153318 A1 | 6/2016 | Busse et al. |
| 2016/0175766 A1 | 6/2016 | Zehnacker et al. |
| 2017/0354921 A1 | 12/2017 | Zehnacker et al. |
| 2017/0354923 A1 | 12/2017 | Zehnacker et al. |
| 2017/0354924 A1 | 12/2017 | Irfan et al. |
| 2017/0355680 A1 | 12/2017 | Wang et al. |
| 2017/0355681 A1 | 12/2017 | Bahlmann et al. |
| 2017/0355682 A1 | 12/2017 | Willy et al. |

FOREIGN PATENT DOCUMENTS

| | | |
|---|---|---|
| CN | 102335545 | 2/2012 |
| DE | 400 488 | 8/1924 |
| DE | 633 146 | 7/1936 |
| DE | 737031 | 7/1943 |
| DE | 36 23 680 A1 | 1/1988 |
| DE | 266 799 A1 | 4/1989 |
| DE | 195 11 709 | 10/1996 |
| DE | 103 33 546 | 2/2005 |
| DE | 10 2004 053 167 | 5/2006 |
| DE | 10 2010 001 070 | 7/2011 |
| DE | 10 2010 004 779 | 7/2011 |
| DE | 10 2011 055 859 | 6/2013 |
| DE | 10 2013 010 035 | 12/2014 |
| DE | 10 2014 214 670 | 1/2016 |
| DE | 10 2014 214 674 | 1/2016 |
| DE | 10 2014 214 682 | 1/2016 |
| DE | 10 2014 110190 | 1/2016 |
| DE | 10 2015 212 749 | 1/2017 |
| DE | 10 2016 210 481 | 6/2017 |
| DE | 10 2016 204 928 | 9/2017 |
| DE | 10 2016 204 929 | 9/2017 |
| DE | 10 2016 204 930 | 9/2017 |
| DE | 10 2016 204 931 | 9/2017 |
| DE | 10 2016 204 932 | 9/2017 |
| DE | 10 2016 204 937 | 9/2017 |
| EP | 0 033 529 A1 | 1/1981 |
| EP | 0 047 967 | 9/1981 |
| EP | 0 079 767 | 5/1983 |
| EP | 0 187 130 | 7/1986 |
| EP | 0 193 327 | 9/1986 |
| EP | 0 302 020 | 2/1989 |
| EP | 0 558 019 | 2/1993 |
| EP | 2 636 715 | 9/2013 |
| FR | 670 497 | 11/1929 |
| FR | 2 900 841 A1 | 11/2007 |
| GB | 1 306 853 | 2/1973 |
| GB | 1 501 195 | 2/1978 |
| GB | 2 047 681 | 12/1980 |
| GB | 2 528 494 | 1/2016 |
| JP | 33-009879 B | 11/1958 |
| JP | 57-191407 | 11/1982 |
| JP | 61-129019 | 6/1986 |
| JP | 62-73055 | 4/1987 |
| JP | 1-134180 | 5/1989 |
| JP | H01-198679 | 8/1989 |
| JP | 2-298767 | 12/1990 |
| JP | 4-268176 | 9/1992 |
| JP | 6-307730 | 11/1994 |
| JP | 7-167521 | 7/1995 |
| JP | 2001-219164 | 8/2001 |
| JP | 2002-047258 | 2/2002 |
| JP | 2004-44945 | 2/2004 |
| JP | 2006-239516 | 9/2006 |
| JP | 2006-282525 | 10/2006 |
| JP | 2010-034301 | 2/2010 |
| JP | 2010-54136 | 3/2010 |
| JP | 2013-051238 | 3/2013 |
| JP | 2013-139425 | 7/2013 |
| RU | 2 101 625 | 1/1998 |
| RU | 2 122 642 | 11/1998 |
| RU | 2 183 003 | 5/2002 |
| WO | WO 93/13367 | 7/1993 |
| WO | WO 00/61698 A1 | 10/2000 |
| WO | WO 2002/016671 | 2/2002 |
| WO | WO 2004/016631 | 2/2004 |
| WO | WO 2004/082809 | 9/2004 |
| WO | WO 2006/012097 | 2/2006 |
| WO | WO 2006/048182 | 5/2006 |
| WO | WO 2007/099041 | 9/2007 |
| WO | WO 2009/032959 | 3/2009 |
| WO | WO 2009/074535 | 6/2009 |
| WO | WO 2009/133059 | 11/2009 |
| WO | WO 2010/037109 | 4/2010 |
| WO | WO 2011/131552 | 10/2011 |
| WO | WO 2012/110987 | 8/2012 |
| WO | WO 2012/150051 | 11/2012 |
| WO | WO 2013/041300 | 3/2013 |
| WO | WO 2013/050230 | 4/2013 |
| WO | WO 2013/050242 | 4/2013 |
| WO | WO 2013/072147 | 5/2013 |
| WO | WO 2015/000637 | 1/2015 |
| WO | WO 2017/005538 | 1/2017 |

OTHER PUBLICATIONS

Krannich, et al., "Characterization of Six Hygroscopic Ionic Liquids with Regard to Their Suitability for Gas Dehydration: Density, Viscosity, Thermal and Oxidative Stability, Vapor Pressure, Diffusion Coefficient, and Activity Coefficient of Water," *Journal of Chemical Engineering & Data 61*:1162-1176 (Feb. 2016).

Kriebel, et al., "Absorption, 2. Design of Systems and Equipment," Ulmann's Encyclopedia of Industrial Chemistry, vol. 1, pp. 75-90 (2008).

Lall-Ramnarine, et al., "Probing the Physical Properties, Synthesis and Cellulose Dissolution Ability of Dialkyl Phosphate Ionic Liquids," *Phosphorous, Sulfur, and Silicon 190*:891-895 (2015).

Lungwitz, Ralf, "Ionische Flüssigkeiten—Polarität and Wechselwirkungen mit silikatischen Oberflächen," Dissertation Technische Universität Chemnitz (Nov. 2011); with English language translation of relevant parts.

English language translation of Mao, et al., "Development and Application of New Technique for Recovery of Low Partial Pressure Carbon Dioxide," *Journal of Chemical Industry & Engineering 25(3)*:12-15 (Jun. 2004).

English language translation of Rolker, et al., "Separation of carbon dioxide from flue gases by means of absorption," *Chemie Ingenieur Tecknik 78(4)*:416-424 (Jul. 2006).

OECD Guidelines for the Testing of Chemicals, Test No. 104, items 14-19, (adopted May 1981).

Projekt der Deutschen Bundesstiftung: Gasreinigung mit ionischen Flüssigkeiten Umwelt; Endbericht (Sep. 2009); with English language translation of relavant parts.

English language translation of Xiao, "Study on Technique for Recovery of Carbon Dioxide from Flue Gas," *Modern Chemical Industry 24(5)*:47-49 (May 2004).

German Search Report dated Feb. 16, 2017 for counterpart German application DE 10 2016 210 483.7 with partial machine translation.

U.S. Appl. No. 14/124,472, filed Dec. 6, 2013, 2014-0090558 A1, Apr. 3, 2014, Rolker.

(56) References Cited

OTHER PUBLICATIONS

U.S. Appl. No. 14/373,350, filed Jul. 19, 2014, 2014-0356268 A1, Dec. 4, 2014, Schraven.
U.S. Appl. No. 14/973,084, filed Dec. 17, 2015, 2016-0175766 A1, Jun. 23, 2016, Zehnacker.
U.S. Appl. No. 15/486,300, filed Apr. 13, 2017, Bahlmann.
U.S. Appl. No. 15/619,561, filed Jun. 12, 2017, Irfan.
U.S. Appl. No. 15/619,566, filed Jun. 12, 2017, Willy.
U.S. Appl. No. 15/619,567, filed Jun. 12, 2017, Wang.
U.S. Appl. No. 15/619,573, filed Jun. 12, 2017, Zehnacker.
U.S. Appl. No. 15/619,577, filed Jun. 12, 2017, Zehnacker.
"Mutual Solubility of Water and Pyridine Derivatives" by Richard M. Stephenson, *J. Chem. Eng. Data 38*, p. 428-431, (Jul. 1993).
"Review of Organic Functional Groups: Introduction to Medicinal Organic Chemistry" by Thomas L. Lemke, Lippincott Williams & Wilkins, p. 40 (2003).
"Review of Organic Functional Groups: Introduction to Medicinal Organic Chemistry" by Thomas L. Lemke, Lippincott Williams & Wilkins, p. 39 (2003).
Brennecke, et al., "Ionic Liquids: Innovative Fluids for Chemical Processing," *AIChE Journal 47*(11):2384-2389 (Nov. 2001).
Chua, et al., "Improved Thermodynamic Property Fields of LiBr—$H_2O$ Solution," *International Journal of Refrigeration 23*:412-429 (Sep. 2000).
De Lucas, et al., "Vapor Pressures, Densities, and Viscosities of the (Water+Lithium Bromide+Lithium Formate) System and (Water+Lithium Bromide+Potassium Formate) System," *Journal of Chemical and Engineering Data, American Chemical Society, US 48(1)*:18-22 (Jan. 2003).
De Lucas, et al., "Absorption of Water Vapor into Working Fluids for Absorption Refrigeration Systems," *Industrial & Engineering Chemistry Research, American Chemical Society, US 46(1)*:345-350 (2007); (published online Dec. 2006).
Domanska, et al., Solubility of 1-Alkyl-3-ethylimidazolium-Based Ionic Liquids in Water and 1-Octanol, *J. Chem. Eng. Data 53*:1126-1132 (Apr. 2008).
Galán, et al., "Solvent Properties of Functionalized Ionic Liquids for $CO_2$ Absorption," *IChemE 85(A1)*:31-39 (Jan. 2007).
Glebov, et al., "Experimental Study of Heat Transfer Additive Influence on the Absorption Chiller Performance," *International Journal of Refrigeration 25*:538-545 (Aug. 2002).
Kim, et al., "Surface tension and viscosity of 1-butyl-3-methylimidazolium iodide and 1-butyl-3-methylimidazolium tetrafluoroborate, and solubility of lithium bromide+1-butyl-3-methylimidazolium bromide in water," *Korean J. Chem. Eng. 23(1)*:113-116 (Jan. 2006).
Kim, et al., "Performance Evaluation of Absorption Chiller Using $LiBr+H_2N(CH_2)_2OH+H_2O$, $LiBr+HO(CH_2)_3OH+H_2O$, and $LiBr+(HOCH_2CH_2NH+H_2O$ as Working Fluids," *Applied Thermal Engineering 19*:217-225 (Feb. 1999).
Kim, et al., "Refractive Index and Heat Capacity of 1-Butyl-3-Methylimidazolium Bromide and 1-Butyl-3-Methylimidazolium Tetrafluoroborate, and Vapor Pressure of Binary Systems for 1-Butyl-3-Methylimidazolium Tetrafluoroborate—Trifluoroethanol," *Fluid Phase Equilibria 218*:215-220 (Apr. 2004).
Li, et al., "Correlation and Prediction of the Solubility of $CO_2$ and $H_2S$ in an Aqueous Solution of 2-Piperidineethanol and Sulfolane," *Ind. Eng. Chem. Res. 37*:3098-3104 (May 1998).
Liu, et al., The physical properties of aqueous solution of room-temperature ionic liquids based on imidazolium:Database and Evaluation, *J. Mol. Liquids 140*:68-72 (Jan. 2008).
Mitsubishi Heavy Industries, Ltd., "Flue Gas $CO_2$ Recovery Technology and Its Application to EOR: an Effective Strategy for Addressing the Issues of Global Warming and Peaking Oil Supply," vol. 44, p. 20-23 (2007).
Perez-Blanco, "A Model of an Ammonia-Water Falling Film Absorber," ASHRAE Transactions vol. 94, pp. 467-483, 1988; Presented at the winter meeting in Dallas Texas of the American Society of Heating, Refrigerating and Air-Conditioning Engineers, Inc. (1988).

Wasserscheid, et al., "Ionic Liquids—New "Solutions" for Transition Metal Catalysis," *Angew. Chem. Int. Ed. 39*:3772-3789 (Nov. 2000).
Wu, et al., "Novel Ionic Liquid Thermal Storage for Solar Thermal Electric Power Systems," *Proceeding of Solar Forum. Solar Energy: The Power to Choose* (Apr. 21-25, 2001).
Yoon, et al., "Cycle Analysis of Air-Cooled Absorption Chiller Using a New Working Solution," *Energy 24*:795-809 (Sep. 1999).
Zhang, et al., "Screening of ionic Liquids to Capture CO2 by COSMO-RS and Experiments," *AIChE Journal 54(10)*:2171-2728 (Oct. 2008).
Zhou, The Vapor Surfactant Theory of Absorption and Condensation Enhancement, *Proc. Int. Sorption Heat Pump Conference*, (Sep. 24-27, 2002).
Ziegler, et al., "Heat-Transfer Enhancement by Additives," *International Journal of Refrigeration 19*:301-309 (Jun. 1996).
Ziegler, et al., "Multi-effect absorption chillers," *Rev. Int. Froid 16(5)*:301-311 (1993).
Ziegler, et al., "Recent developments and future prospects of sorption heat pump systems," *Int. J. Therm. Sci. 38*:191-208 (Mar. 1999).
Blachly, et al., "Stabilization of Monoethanolmine Solutions in Carbon Dioxide Scrubbers," *J. Chem. Eng. Data 11(3)*:401-403 (Jul. 1966).
Call,"Aminoxyle—eine Klasse stabiler," *Pharmazie in unserer Zeit 3*:83-95 (Jan. 1977); with English language translation attached.
Kirchhoff, et al., "Triacetoneamine Derivatives Industrial Applications and Recent Developments," pp. 1-9, Addcon World '99 (Two-Day Conference, Oct. 1999).
Lewin, et al., "Molecular Features Associated with Polyamine Modulation of NMDA Receptors," *J. Med. Chem. 41*:988-995 (published online Feb. 1998).
Luo, et al., "Dehumidification performance of [EMIM]$BF_4$," *Applied Thermal Engineering 31(14-15)*:2772-2777 (Oct. 2011).
Luo, et al., "Investigation of feasibility of ionic liquids used in solar liquid desiccant air conditioning system," *Solar Energy 86(9)*:2781-2724 (Sep. 2012).
Satori, et al., "Sterically Hindered Amines for $CO_2$ Removal from Gases," *Ind. Eng. Chem. Fundam. 22(2)*:239-249 (accepted Jan. 1983).
Gerald Scott, Develpoments in polymer stabilization-5, Chapter 3: Antioxidant action of sterically hindered amines and related compounds, Shlyapintokh and Ivanor; pp. 41-70, Applied Science Publishers (1982).
Shao & Stangeland, "Amines Used in $CO_2$ Capture—Health and Environmental Impacts," Bellona Report (Sep. 2009).
Ulmann's Encyclopedia of Industrial Chemistry, 5th Edition, vol. 83, "Antioxidants" pp. 91-104 (1985).
Wellner, et al., "Entwässerung ionischer Flüssigkeiten in einem Fallfilmverdampfer," *Chemie Ingenieur Technik 83(9)*:1493-1501(Jul. 2011); with complete English language translation.
Yunus, "Gaslöslichkeit in ionischen Flüssigkeiten," IsoSORP Application Note Nr. 4:1-2 (Feb. 2014); with complete English language translation.
Encylopedia of Chemical Process and Design, Ed. John J. McKetta, vol. 32. Marcel Deckker, Inc. (1990) pp. 123-126.
English language translation of the German Search Report for corresponding German application DE 10 2016 210 483.7, filed Jun. 14, 2016.
English language translation of Singaporian Written Opinion for corresponding Singapore application 10201704816R, filed Jun. 12, 2017.
Kuhlmann, et al., "Imidazolium dialkylphosphates—a class of versatile, halogen-free and hydrolytically stable ionic liquids," *Green Chem. 9*:233-242 (2007).
Li, et al., "Efficient absorption of ammonia with hydroxyl-functionalized ionic liquids," *RCS Adv. 5*:81362-81370 (2015).
U.S. Appl. No. 15/742,436, filed Jan. 5, 2018, Zehnacker.

* cited by examiner

PROCESS AND ABSORBENT FOR DEHUMIDIFYING MOIST GAS MIXTURES

CROSS REFERENCE TO RELATED APPLICATIONS

The present application claims priority under 35 USC § 119 to German application, DE 10 2016 210 483.7, filed on Jun. 14, 2016, the contents of which is incorporated herein by reference in its entirety.

FIELD OF THE INVENTION

The invention relates to a process for dehumidifying a moist gas mixture in which the moist gas mixtures are brought into contact with an absorbent comprising dialkylimidazolium salts and trialkyl phosphate. In addition, the invention also relates to an absorption heat pump comprising the absorbent according to the invention and to the absorbent according to the invention itself.

BACKGROUND OF THE INVENTION

Dehumidification of moist gas mixtures is necessary in a multitude of technical fields. For instance, ventilation and air conditioning of buildings or vehicles generally necessitates not only cooling but also dehumidification of the air since the air to be cooled is often so humid that during cooling to the desired temperature the temperature falls below the dew point temperature. Hence in conventional air conditioning systems dehumidification of the air accounts for a large part of the electricity consumption.

The electricity consumption of air conditioning systems for buildings is reduced by dehumidifying the air by adsorption or absorption of water with a drying medium and subsequently regenerating the water-laden drying medium by heating to a temperature at which the water is desorbed again. Compared to adsorption on a solid adsorbent, the advantage of absorption in a liquid absorption medium is that air dehumidification can be carried out with reduced equipment complexity and with less drying medium and that regeneration of the water-laden drying medium is easier to carry out using solar heat.

A further technical field where dehumidification of moist gas mixtures is employed is the field of absorption chillers (principle described in WO 2014/079675 A1; "absorption chiller" is used synonymously with "absorption heat pump" according to the invention). Here, the moist gas mixture is formed during evaporation of water under low pressure. The water vapour thus formed needs to be removed from the moist gas mixture so that said mixture may then be returned to the water evaporation to pass through a new cycle. Here too, absorption in a liquid absorption medium is favoured over adsorption on a solid adsorption medium.

In addition to use in absorption chillers, there is still a further area in which the drying of gas streams is necessary. This is natural gas refinement, which applies other requirements on the ionic liquids to be used therefor.

To absorb moisture with the aid of ionic liquids, the prior art proposes a series of ionic liquids. Thus, DE 10 2010 004 779 A1 mentions 1-ethyl-3-methylimidazolium ethylsulphate, 1-ethyl-3-methylimidazolium methylsulphate, 1-ethyl-3-methylimidazolium diethylphosphate, 1-ethyl-3-methylimidazolium methylsulphonate, 1-butyl-3-methylimidazolium bistrifluoromethanesulphonimide, 1-butyl-3-ethylimidazolium chloride for example.

CN 102335545 A describes a series of ionic liquids based on alkyl phosphates, namely inter alia 1,3-dimethyimidazolium dimethylphosphate, 1-ethyl-3-methylimidazolium dimethylphosphate and 1-butyl-3-methylimidazolium dimethylphosphate.

Y. Luo et al., Appl. Thermal Eng. 31 (2011) 2772-2777 proposes using the ionic liquid 1-ethyl-3-methylimidazolium tetrafluoroborate in place of aqueous solutions of lithium bromide for air dehumidification. However, this ionic liquid has the disadvantage of only poor absorption capability.

Y. Luo et al., Solar Energy 86 (2012) 2718-2724 proposes the ionic liquid 1,3-dimethyimidazolium acetate as an alternative to 1-ethyl-3-methylimidazolium tetrafluoroborate for air dehumidification. The acetates are also discussed by M. Kanakubo et al., J. Mol. Liq. 217 (2016) 112-119.

US 2011/0247494 A1 proposes a further ionic liquid for this purpose, namely 1-ethyl-3-methylimidazolium acetate.

The application of these ionic liquids in absorption chillers is also discussed in WO 2013/050242 A1.

While these ionic liquids described in the prior art are very well-suited for dehumidification, the ionic liquids, which include dialkylimidazolium ions, exhibit the disadvantage that, especially on contact with gas mixtures, chemicals are given off which lead to olfactory contamination of the ambient air. This is especially the case on dehumidification of indoor air and is undesirable in the case of absorption chillers such as refrigerators. Therefore, an absorbent is sought with which this contamination can be minimized.

For this reason, the object of the present invention consisted of providing an absorbent in which the tendency to give off badly odorous substances therefrom is particularly low. An absorption medium which achieves this object has now surprisingly been found.

DETAILED DESCRIPTION OF THE INVENTION

Accordingly, the present invention relates to a process for dehumidifying a moist gas mixture $G_1$, wherein the moist gas mixture $G_1$ is contacted with a liquid absorption medium $A_1$, which comprises a mixture of at least one trialkyl phosphate of structure (I)

and at least one salt S selected from the group consisting of $Q^+A^-$, $Q^+(R^1O)_2PO_2^-$, $(Q^+)_2R^2OPO_3^{2-}$, $Q^+M^+ R^3OPO_3^{2-}$, to obtain a gas mixture $G_2$ which has a lower water content compared to the moist gas mixture $G_1$ and a liquid absorption medium $A_2$ which has an elevated water content compared to the liquid absorption medium $A_1$, wherein $Q^+$ is a dialkylimidazolium cation and in which in particular the alkyl groups each independently have 1 to 10 carbon atoms, wherein $A^-$ is an anion selected from the group consisting of $R*COO^-$, $R'SO_3^-$, $HSO_4^-$, $R''SO_4^-$, where $R*$, $R'$, $R''$, $R^A$, $R^B$, $R^C$ are each independently an alkyl group, in particular having 1 to 10 carbon atoms, where $R^1$, $R^2$, $R^3$ are each independently an alkyl group, in particular having 1 to 10 carbon atoms, and where $M^+$ is an alkali metal ion, preferably $Li^+$, $K^+$ or $Na^+$, more preferably $K^+$ or $Na^+$, "Moist" is to be understood as meaning in the context of the invention "comprising water, in particular water vapour".

"Dehumidifying" is to be understood as meaning "at least partially removing water".

"At least partially" is to be understood as meaning in the context of the invention "partially or completely".

"Moist gas mixture $G_1$" is accordingly to be understood as meaning in the context of the invention that the gas mixture $G_1$ comprises water, preferably water vapour ("water vapour" is to be understood as meaning water in the gaseous physical state), and that its composition is otherwise not subject to any particular restrictions. The water content of the moist gas mixture is not subject to any particular restrictions and is in particular from 0.01 vol % to 99.99 vol % ("vol %" indicates the volume of water vapour based on the overall volume of the moist gas mixture $G_1$). The composition of the moist gas mixture $G_1$ may otherwise vary depending on the application of the process according to the invention. The moist gas mixture $G_1$ is in particular selected from moist natural gas, moist air (this may be moist indoor air or the moist air resulting from evaporation of water in absorption chillers), preferably moist air. For moist natural gas the water content is in particular from 0.01 vol % to 15.00 vol %, for moist air said content is in particular from 0.01 vol % to 15.00 vol % in the case of moist indoor air or in particular from 95.00 vol % to 99.99 vol % which is the preferred range when moist air resulting from evaporation of water in absorption chillers is concerned.

The moist gas mixture $G_1$ used in the process has in particular a temperature of 2° C. to 100° C., preferably 3° C. to 60° C., more preferably 4° C. to 50° C., even more preferably 5° C. to 40° C. and is otherwise not subject to any particular restrictions. However, since the absorption capacity in this temperature range is so good, the process according to the invention is particularly well-suited for dehumidifying natural gas wherein processing of said gas often occurs in this temperature range.

In the process according to the invention, the absorption medium $A_1$ preferably also has a temperature of 10° C. to 100° C., preferably 15° C. to 80° C., more preferably 20° C. to 50° C., even more preferably 20° C. to 30° C.

The contacting may be effected in any way known to those skilled in the art, in particular in a water absorption unit $W_{abs1}$ (elucidated below). The contacting causes the absorption medium $A_1$ to at least partially absorb moisture, i.e. water, from the moist gas stream gas mixture $G_1$.

The process according to the invention is in particular carried out in an apparatus $V_1$. The apparatus $V_1$ is restricted only to the extent that it shall be suitable for carrying out the process according to the invention. In particular, an apparatus $V_1$ comprising the following components may be employed:
(i) at least one water absorption unit $W_{abs1}$ set up for contacting the moist gas mixture with the liquid absorption medium, in particular $A_1$.

Apparatus $V_1$ also optionally comprises the following components:
(ii) at least one water desorption unit $W_{abs1}$ which comprises a heat exchanger $W_{x1}$ and which is set up for at least partially removing water from a liquid absorption medium, in particular $A_2$,
(iii) and a circuit $U_1$, which connects the water absorption unit $W_{abs1}$ with the water desorption unit $W_{des1}$ and by means of which the liquid absorption medium, in particular $A_1$ and $A_2$, may be circulated.

The process according to the invention may accordingly be carried out in a water absorption unit $W_{abs1}$ familiar to the person skilled in the art. Employable water absorption units $W_{abs1}$ include in particular the water absorbers known to those skilled in the art. Said absorbers are based on the principle of increasing the surface area of the liquid absorption medium $A_1$ and simultaneously achieving the longest possible residence time of the liquid absorption medium $A_1$ in the water absorber during absorption of water. It is in particular possible here to employ water absorbers selected from the group of: packed beds, spray columns, falling-films, bubble columns, tray columns, wet scrubbers (for example Venturi scrubbers), stirred tanks and combinations of these absorbers. It is particularly preferable to employ falling-films, in particular shell and tube falling-films, as water absorbers. The water absorption unit $W_{abs1}$ may in particular also comprise an additional heat exchanger $W_{z1}$ set up such that the liquid absorption medium $A_1$ is adjustable to the desired temperature.

In a water desorption unit $W_{des1}$, which comprises a heat exchanger $W_{x1}$, the same can again be withdrawn to the water-laden liquid absorption medium, in particular $A_2$. The water desorption unit $W_{des1}$ is based on the principle of supplying heat to the water-laden liquid absorption medium, in particular $A_2$, increasing the surface area of the water-laden liquid absorption medium $A_1$ and simultaneously achieving the longest possible residence time of the water-laden liquid absorption medium, in particular $A_2$, in the water desorption unit $W_{des1}$.

Employable water desorption units $W_{des1}$ comprising a heat exchanger $W_{x1}$ include in particular the combinations of heat exchanger and water desorber known to those skilled in the art, in particular horizontal tube evaporators having an upstream heat exchanger, in particular shell and tube heat exchangers, plate and frame heat exchangers. In addition, the water desorption unit $W_{des1}$ comprising a heat exchanger $W_{x1}$ may also be a water desorber having an integrated heat exchanger. Such water desorbers having an integrated heat exchanger are in particular climbing film evaporators, long tube vertical evaporators, short tube vertical evaporators, forced circulation evaporators, agitated thin film evaporators. It is particularly preferable to employ falling-films, in particular shell and tube falling-films, as water desorption unit $W_{des1}$.

In the circuit $U_1$, in particular the water-laden liquid absorption medium $A_2$ from the water absorption unit $W_{abs1}$ is conducted to the water desorption unit $W_{des1}$ and even more preferably—particularly when the process according to the invention is carried out continuously—liquid absorbent from the water desorption unit $W_{des1}$ is conducted to the water absorption unit $W_{abs1}$.

The circuit $U_1$ is in particular a conduit, in particular selected from the group consisting of tube, hose.

In a further preferred embodiment the circuit $U_1$ also comprises a pump.

It is preferable to cool the absorption medium $A_1$ during contacting of the moist gas mixture $G_1$ in order that as much moisture as possible is absorbed from the moist gas mixture $G_1$. This may be achieved, for example, via an additional heat exchanger $W_{z1}$ in the water absorption unit $W_{abs1}$.

In the process according to the invention, the moist gas mixture $G_1$ is contacted with a liquid absorption medium $A_1$, which comprises a mixture of at least one trialkyl phosphate of structure (I)

(I)

and at least one salt S selected from the group consisting of $Q^+A^-$, $Q^+(R^1O)_2PO_2^-$, $(Q^+)_2R^2OPO_3^{2-}$, $Q^+M^+R^3OPO_3^{2-}$, to obtain a gas mixture $G_2$ which has a lower water content compared to the moist gas mixture $G_1$ and a liquid absorption medium $A_2$ which has an elevated water content compared to the liquid absorption medium $A_1$, where $Q^+$ is a dialkylimidazolium cation, in which in particular the alkyl groups each independently have 1 to 10, preferably 1 to 8, more preferably 1 to 6, still more preferably 1 to 4, even more preferably 1 or 2 carbon atoms, where $A^-$ is an anion selected from the group consisting of $R^*COO^-$, $R'SO_3^-$, $HSO_4^-$, $R''SO_4^-$, where $R^*$, $R'$, $R''$, $R^A$, $R^B$, $R^C$, $R^1$, $R^2$, $R^3$ are each independently an alkyl group, in particular having 1 to 10, preferably 1 to 8, more preferably 1 to 6, still more preferably 1 to 4, even more preferably 1 or 2 carbon atoms, and where $M^+$ is an alkali metal ion, preferably $Li^+$, $K^+$ or $Na^+$, more preferably $K^+$ or $Na^+$.

In a preferred embodiment of the process according to the invention the salt S is selected from the group consisting of $Q^+A^-$, $Q^+(R^1O)_2PO_2^-$, and $Q^+$ is a dialkylimidazolium cation, in which the alkyl groups each independently have 1 to 6, preferably 1 to 4, more preferably 1 or 2 carbon atoms, and $A^-$ is an anion selected from the group consisting of $R^*COO^-$, $R'SO_3^-$, $R''SO_4^-$, where $R^*$, $R^1$, $R'$, $R''$, $R^A$, $R^B$, $R^C$ are each independently an alkyl group having 1 to 6, preferably 1 to 4, more preferably 1 or 2 carbon atoms.

In a more preferred embodiment of the process according to the invention, the salt S has the general formula $Q^+(R^1O)_2PO_2^-$, and $Q^+$ is a dialkylimidazolium cation, in which the alkyl groups are each independently methyl or ethyl, and $R^1$, $R^A$, $R^B$, $R^C$ are each independently methyl or ethyl.

In a still more preferred embodiment of the process according to the invention, the salt S has the general formula $Q^+(R^1O)_2PO_2^-$, and $Q^+$ is selected from the group consisting of 1,3-dimethylimidazolium, 1,3-diethylimidazolium, 1-ethyl-3-methylimidazolium, and $R^A$, $R^B$, $R^C$, are each independently methyl or ethyl. Even more preferably, $Q^+$ is then 1-ethyl-3-methylimidazolium and $R^A$, $R^B$, $R^C$, $R^1$ are each independently methyl or ethyl.

Furthermore, in all the aforementioned embodiments of the process according to the invention, it is particularly preferred if $R^A$, $R^B$, $R^C$ are each independently selected from methyl, ethyl, more preferably $R^A=R^B=R^C=$methyl or $R^A=R^B=R^C=$ethyl, particularly preferably $R^A=R^B=R^C=$ethyl.

The liquid absorption medium $A_1$ may be employed in the process according to the invention in the form of the pure mixture of the trialkyl phosphates of structure (I) and the salts S. Alternatively and more preferably in the process according to the invention, the liquid absorption medium $A_1$ is an aqueous solution, in which in particular the total weight of all trialkyl phosphates of structure (I) and all salts S is in the range of 65% by weight to 95% by weight, based on the total weight of the aqueous solution. Still more preferably, the total weight of all trialkyl phosphates of structure (I) and all salts S in $A_1$ is in the range of 70% by weight to 90% by weight, based on the total weight of the aqueous solution, even more preferably in the range of 75% by weight to 87% by weight. In the process according to the invention, the ratio of all trialkyl phosphates of structure (I) to the salts S in the absorption medium $A_1$ is not subject to any further restrictions. However, it is preferable to employ in the process according to the invention an absorption medium $A_1$ in which the ratio of the total weight of all trialkyl phosphates of structure (I) to the total weight of all salts S is in the range 1:9999 to 1:9, more preferably 1:9999 to 1:99, yet more preferably 1:9999 to 1:999. The gas mixture $G_2$ obtained in the process according to the invention, which has a lower water content compared to the moist gas mixture $G_1$, then represents the dehumidified gas stream which, in the case of dehumidified natural gas, can be supplied to power generation.

The liquid absorption medium $A_2$ obtained in the process according to the invention has an elevated water content compared to the liquid absorption medium $A_1$. It will be appreciated that in terms of the salts S comprised by it and in terms of the trialkyl phosphates of structure (I) comprised by it, $A_2$ is identical to $A_1$ and is preferably distinguished therefrom only by its water content.

In a preferred embodiment of the process according to the invention, in a further step ["optional step b)", wherein the process according to the invention is to be understood in this context as "step a)"], the at least partial removal of water from the liquid absorption medium $A_2$ to obtain a liquid absorption medium $A_3$ having a lower water content compared to the liquid absorption medium $A_2$ is then effected. Heat is additionally supplied to the liquid absorption medium $A_2$ here. The supply of heat and the at least partial removal may be effected in any way known to those skilled in the art, in particular in a water desorption unit $W_{des1}$ comprising a heat exchanger $W_{x1}$. The at least partial removal of water from the liquid absorption medium $A_2$ affords a liquid absorption medium $A_3$ having a lower water content compared to the liquid absorption medium $A_2$.

It will be appreciated that in terms of the salts S comprised by it and in terms of the trialkyl phosphates of structure (I) comprised by it, the liquid absorption medium $A_3$ is identical to $A_2$ and is preferably distinguished therefrom only by its water content.

In a further preferred embodiment the process according to the invention is carried out in continuous fashion. This is to be understood as meaning in particular that following step b) the steps a) and b) are performed at least one more time and that the liquid absorption medium $A_1$ employed in the steps a) additionally performed in each case is at least partially the liquid absorption medium $A_3$ obtained from the step b) performed immediately beforehand, i.e. in particular the water content of the liquid absorption medium $A_1$ employed in the step a) additionally performed in each case and of the liquid absorption medium $A_3$ from the immediately preceding step b) are identical.

It is yet more preferable when in this embodiment liquid absorption medium $A_2$ is supplied with heat from liquid absorption medium $A_3$. This may be carried out in an additional heat exchanger $W_{y1}$, in particular selected from the group consisting of shell and tube heat exchangers and plate and frame heat exchangers. This makes it possible to carry out the process according to the invention in a particularly energy efficient fashion.

The invention also relates in a further aspect to an apparatus $V_2$ for dehumidifying a moist gas mixture, in particular moist air, comprising the components:

(i) a liquid absorption medium $A_{1*}$, which comprises a mixture of at least one trialkyl phosphate of structure (I)

and at least one salt S selected from the group consisting of $Q^+A^-$, $Q^+(R^1O)_2PO_2^-$, $(Q^+)_2R^2OPO_3^{2-}$, $Q^+M^+R^3OPO_3^{2-}$, (ii) at least one water absorption unit $W_{abs2}$ set up for contacting the moist gas mixture with the liquid absorption medium $A_{1*}$, (iii) at least one water desorption unit $W_{des2}$ which comprises a heat exchanger $W_{x2}$ and is set up for at least partially removing water from a liquid absorption medium $A_{1*}$, (iv) and a circuit $U_2$ which connects the water absorption unit $W_{abs2}$ with the water desorption unit $W_{des2}$ and by means of which the liquid absorption medium $A_{1*}$ may be circulated, characterized in that $Q^+$ is a dialkylimidazolium cation, in which in particular the alkyl groups each independently have 1 to 10, preferably 1 to 8, more preferably 1 to 6, still more preferably 1 to 4, even more preferably 1 or 2 carbon atoms, where $A^-$ is an anion selected from the group consisting of $R*COO^-$, $R'SO_3^-$, $HSO_4^-$, $R''SO_4^-$, where $R*$, $R'$, $R''$, $R^A$, $R^B$, $R^C$, $R^1$, $R^2$, $R^3$ are each independently an alkyl group, in particular having 1 to 10, preferably 1 to 8, more preferably 1 to 6, still more preferably 1 to 4, even more preferably 1 or 2 carbon atoms, and where Mt is an alkali metal ion, preferably $Li^+$, $K^+$, or $Na^+$, more preferably $K^+$ or $Na^+$.

The apparatus $V_2$ according to the invention is suitable for dehumidifying a moist gas mixture, in particular moist air. Said apparatus comprises the following components:

As first component, the apparatus $V_2$ according to the invention comprises a liquid absorption medium $A_{1*}$, which comprises a mixture of at least one trialkyl phosphate of structure (I)

and at least one salt S selected from the group consisting of $Q^+A^-$, $Q^+(R^1O)_2PO_2^-$, $(Q^+)_2R^2OPO_3^{2-}$, $Q^+M^+R^3OPO_3^{2-}$, $Q^+$ is a dialkylimidazolium cation, in which in particular the alkyl groups each independently have 1 to 10, preferably 1 to 8, more preferably 1 to 6, still more preferably 1 to 4, even more preferably 1 or 2 carbon atoms, where $A^-$ is an anion selected from the group consisting of $R*COO^-$, $R'SO_3^-$, $HSO_4^-$, $R''SO_4^-$, where $R*$, $R'$, $R''$, $R^A$, $R^B$, $R^C$, $R^1$, $R^2$, $R^3$ are each independently an alkyl group, in particular having 1 to 10, preferably 1 to 8, more preferably 1 to 6, still more preferably 1 to 4, even more preferably 1 or 2 carbon atoms, and where $M^+$ is an alkali metal ion, preferably $Li^+$, $K^+$ or $Na^+$, more preferably $K^+$ or $Na^+$.

In a preferred embodiment of the apparatus $V_2$ according to the invention, in $A_{1*}$ the salt S is selected from the group consisting of $Q^+A^-$, $Q^+(R^1O)_2PO_2^-$, and $Q^+$ is a dialkylimidazolium cation, in which the alkyl groups each independently have 1 to 6, preferably 1 to 4, more preferably 1 or 2 carbon atoms, and $A^-$ is an anion selected from the group consisting of $R*COO^-$, $R'SO_3^-$, $R''SO_4^-$, where $R*$, $R^1$, $R''$, $R^A$, $R^B$, $R^C$ are each independently an alkyl group having 1 to 6, preferably 1 to 4, more preferably 1 or 2 carbon atoms.

In a more preferred embodiment of the apparatus $V_2$ according to the invention, in $A_{1*}$ the salt S has the general formula $Q^+(R^1O)_2PO_2^-$, and $Q^+$ is a dialkylimidazolium cation, in which the alkyl groups are each independently methyl or ethyl, and $R^1$, $R^A$, $R^B$, $R^C$ are each independently methyl or ethyl.

In a still more preferred embodiment of the apparatus $V_2$ according to the invention, in $A_{1*}$ the salt S has the general formula $Q^+(R^1O)_2PO_2^-$, and $Q^+$ is selected from the group consisting of 1,3-dimethylimidazolium, 1,3-diethylimidazolium, 1-ethyl-3-methylimidazolium, and $R^A$, $R^B$, $R^C$, $R^1$ are each independently methyl or ethyl. Even more preferably, $Q^+$ is then 1-ethyl-3-methylimidazolium and $R^A$, $R^B$, $R^C$, $R^1$ are each independently methyl or ethyl.

Furthermore, in all the aforementioned embodiments of the apparatus $V_2$ according to the invention, it is particularly preferred if in $A_{1*}$ $R^A$, $R^B$, $R^C$ are each independently selected from methyl, ethyl, more preferably $R^A=R^B=R^C=$methyl or $R^A=R^B=R^C=$ethyl, particularly preferably $R^A=R^B=R^C=$ethyl.

The liquid absorption medium $A_{1*}$ may be employed in the process according to the invention in the form of the pure mixture of the trialkyl phosphates of structure (I) and the salts S. Alternatively and more preferably, in the process according to the invention the liquid absorption medium $A_{1*}$ is an aqueous solution, in which in particular the total weight of all trialkyl phosphates of structure (I) and all salts S is in the range of 65% by weight to 95% by weight, based on the total weight of the aqueous solution. Still more preferably, the total weight of all trialkyl phosphates of structure (I) and all salts S in $A_{1*}$ is in the range of 70% by weight to 90% by weight, based on the total weight of the aqueous solution, even more preferably in the range of 75% by weight to 87% by weight.

The ratio of all trialkyl phosphates of structure (I) to the salts S in the liquid absorption medium $A_{1*}$ is not subject to any further restrictions. However, it is preferable to employ an absorption medium $A_{1*}$ in the apparatus $V_2$ according to the invention in which the ratio of the total weight of all trialkyl phosphates of structure (I) to the total weight of all salts S is in the range 1:9999 to 1:9, more preferably 1:9999 to 1:99, even more preferably 1:9999 to 1:999.

As a second component the apparatus $V_2$ according to the invention comprises a water absorption unit $W_{abs2}$ set up for contacting the moist gas mixture with the liquid absorption medium $A_{1*}$. The water absorption unit $W_{abs2}$ may in particular comprise an additional heat exchanger $W_{z2}$ set up such that the liquid absorption medium $A_{1*}$ is coolable. Employable water absorption units $W_{abs2}$ of this kind include in particular the water absorbers known to those skilled in the art. Said absorbers are based on the principle of increasing the surface area of the liquid absorption medium $A_{1*}$ and simultaneously achieving the longest possible residence time of the liquid absorption medium $A_{1*}$ in the water absorber during absorption of water. It is in particular possible here to employ water absorbers selected from the group of: packed beds, spray columns, falling-films, bubble columns, tray columns, wet scrubbers (for example Venturi scrubbers), stirred tanks and combinations of these absorbers. It is particularly preferable to employ falling-films, in particular shell and tube falling-films, as water absorbers.

As a third component the apparatus $V_2$ according to the invention comprises a water desorption unit $W_{des2}$ which comprises a heat exchanger $W_{x2}$ and is set up for at least partially removing water from the liquid absorption medium $A_{1*}$. Particularly the combinations of heat exchanger and water desorber known to those skilled in the art may be employed therefor. The water desorption unit $W_{des2}$ is based on the principle of supplying heat to the liquid absorption medium $A_{1*}$, increasing the surface area of the liquid absorption medium $A_{1*}$ and simultaneously achieving the longest possible residence time of the liquid absorption medium $A_{1*}$ in the water desorption unit.

Employable water desorption units $W_{des2}$ comprising a heat exchanger $W_{x2}$ include in particular the combinations of heat exchanger and water desorber known to those skilled in the art, in particular horizontal tube evaporators having an upstream heat exchanger, in particular shell and tube heat exchangers, plate and frame heat exchangers. In addition, the water desorption unit $W_{des2}$ comprising a heat exchanger $W_{x2}$ may also be a water desorber having an integrated heat exchanger. Such water desorbers having an integrated heat exchanger are in particular climbing film evaporators, long tube vertical evaporators, short tube vertical evaporators, forced circulation evaporators, agitated thin film evaporators. It is particularly preferable to employ as water desorption unit $W_{des2}$ falling-films, in particular shell and tube falling-films.

As a fourth component the apparatus $V_2$ according to the invention comprises a circuit $U_2$ which connects the water absorption unit $W_{abs2}$ with the water desorption unit $W_{des2}$ and by means of which the liquid absorption medium $A_{1*}$ may be circulated. The circuit $U_2$ is preferably a conduit, more preferably selected from the group consisting of tube, hose. In a further preferred embodiment the circuit $U_2$ also comprises a pump.

In a preferred embodiment the apparatus $V_2$ comprises a further heat exchanger $W_{y2}$ (additional to the heat exchanger $W_{x2}$ comprised in the water desorption unit $W_{des2}$). The heat exchanger $W_{y2}$ is set up such that liquid absorption medium $A_{1*}$ sent from the water absorption unit $W_{abs2}$ to the water desorption unit $W_{des2}$ may be supplied with heat from liquid absorption medium $A_{1*}$, said medium being conducted away from the water desorption unit $W_{des2}$. This can be ensure by employing as heat exchanger $W_{y2}$ in particular a heat exchanger selected from shell and tube heat exchangers, plate and frame heat exchangers.

In a further preferred embodiment, the apparatus $V_2$ is part of an absorption heat pump. This absorption heat pump then comprises as further components a condenser, an evaporator and a coolant, wherein the coolant is water.

The condenser is in particular connected to the water desorption unit $W_{des2}$ via a conduit and is set up for condensing water at least partially removed from the liquid absorption medium $A_{1*}$ in the water desorption unit $W_{des2}$. The condenser preferably also comprises a cooling water circuit.

The evaporator is in particular connected to the condenser via a conduit (which may comprise a throttling means) and connected to the water absorption unit $W_{abs2}$ via a further conduit and is set up for evaporating condensed water from the condenser. The evaporator preferably also comprises a pressure of <1 bar, more preferably <0.1 bar, to permit evaporation of the condensed water at the lowest possible temperatures. The evaporator may further preferably additionally comprise an apparatus from which heat may be drawn and so that the condensed water may be evaporated (for example a coolant conduit in which coolant is passed into the space in which water is evaporated).

Finally, the present invention also relates to the absorption medium $A_{1*}$ itself, in which the absorption medium $A_{1*}$ comprises a mixture of at least one trialkyl phosphate of structure (I)

(I)

and at least one salt S selected from the group consisting of $Q^+A^-$, $Q^+(R^1O)_2PO_2^-$, $(Q^+)_2R^2OPO_3^{2-}$, $Q^+M^+R^3OPO_3^{2-}$, where $Q^+$ is a dialkylimidazolium cation, in which in particular the alkyl groups each independently have 1 to 10, preferably 1 to 8, more preferably 1 to 6, still more preferably 1 to 4, even more preferably 1 or 2 carbon atoms, where $A^-$ is an anion selected from the group consisting of $R^*COO^-$, $R'SO_3^-$, $HSO_4^-$, $R''SO_4^-$, where $R^*$, $R'$, $R''$, $R^A$, $R^B$, $R^C$, $R^1$, $R^2$, $R^3$ are each independently an alkyl group, in particular having 1 to 10, preferably 1 to 8, more preferably 1 to 6, still more preferably 1 to 4, even more preferably 1 or 2 carbon atoms, and where $M^+$ is an alkali metal ion, preferably $Li^+$, $K^+$ or $Na^+$, more preferably $K^+$ or $Na^+$.

In a preferred embodiment of the absorption medium $A_{1*}$ according to the invention, in said medium the salt S is selected from the group consisting of $Q^+A^-$, $Q^+(R^1O)_2PO_2^-$, and $Q^+$ is a dialkylimidazolium cation, in which the alkyl groups each independently have 1 to 6, preferably 1 to 4, more preferably 1 or 2 carbon atoms, and $A^-$ is an anion selected from the group consisting of $R^*COO^-$, $R'SO_3^-$, $R''SO_4^-$ where $R^*$, $R^1$, $R'$, $R''$, $R^A$, $R^B$, $R^C$ are each independently an alkyl group having 1 to 6, preferably 1 to 4, more preferably 1 or 2 carbon atoms.

In a more preferred embodiment of the absorption medium $A_1$ according to the invention, in said medium the salt S has the general formula $Q^+(R^1O)_2PO_2^-$, and $Q^+$ is a dialkylimidazolium cation, in which the alkyl groups are each independently methyl or ethyl, and $R^1$, $R^A$, $R^B$, $R^C$ are each independently methyl or ethyl.

In a still more preferred embodiment of the absorption medium $A_1$ according to the invention, in said medium the salt S has the general formula $Q^+(R^1O)_2PO_2^-$, and $Q^+$ is selected from the group consisting of 1,3-dimethylimidazolium, 1,3-diethylimidazolium, 1-ethyl-3-methylimidazolium, and $R^A$, $R^B$, $R^C$ are each independently methyl or ethyl. Even more preferably, $Q^+$ is then 1-ethyl-3-methylimidazolium and $R^A$, $R^B$, $R^C$, $R^1$ are each independently methyl or ethyl.

Furthermore, in all the aforementioned embodiments of the absorption medium $A_{1*}$ according to the invention, it is particularly preferred if in $A_{1*}$ $R^A$, $R^B$, $R^C$ are each independently selected from methyl, ethyl, more preferably $R^A=R^B=R^C=$methyl or $R^A=R^B=R^C=$ethyl, particularly preferably $R^A=R^B=R^C=$ethyl.

The liquid absorption medium $A_{1*}$ may be present in the form of the pure mixture of the trialkyl phosphates of structure (I) and the salts S. Alternatively and more preferably, the liquid absorption medium $A_{1*}$ is an aqueous solution, in which in particular the total weight of all trialkyl phosphates of structure (I) and all salts S is in the range of 65% by weight to 95% by weight, based on the total weight of the aqueous solution. Still more preferably, the total weight of all trialkyl phosphates of structure (I) and all salts S in $A_{1*}$ is in the range of 70% by weight to 90% by weight, based on the total weight of the aqueous solution, even more preferably in the range of 75% by weight to 87% by weight.

The ratio of all trialkyl phosphates of structure (I) to the salts S in the liquid absorption medium $A_{1*}$ is not subject to any further restrictions. In the liquid absorption medium $A_{1*}$, the ratio of the total weight of all trialkyl phosphates of structure (I) to the total weight of all salts S is preferably in the range of 1:9999 to 1:9, more preferably 1:9999 to 1:99, yet more preferably 1:9999 to 1:999.

Figure 1:
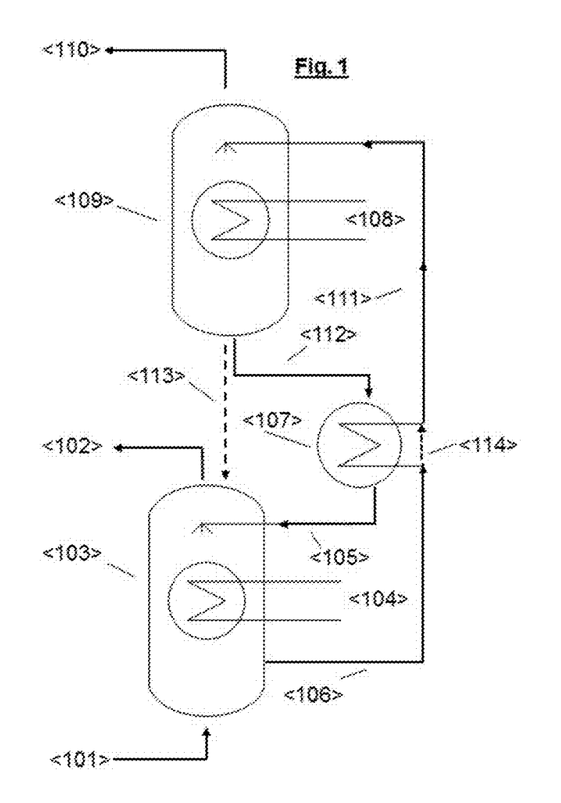
FIG. 1 (abbreviated to "FIG. 1") shows an embodiment of apparatus $V_2/V_1$ according to the invention.
Figure 2:
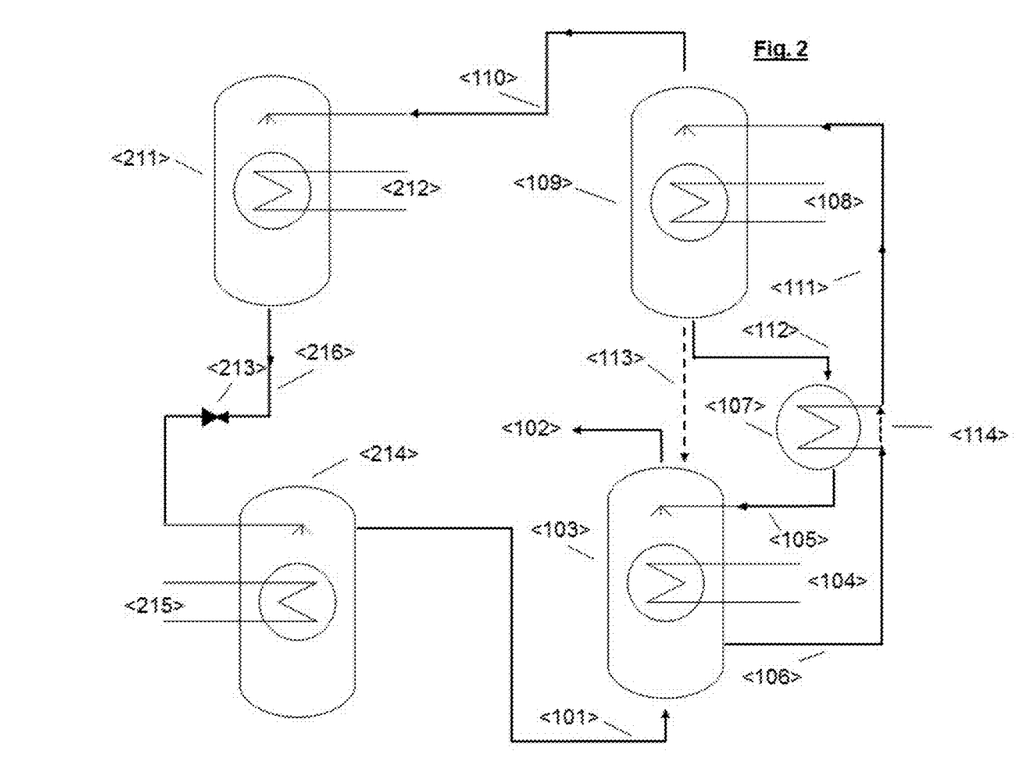
FIG. 2 (abbreviated as "FIG. 2") shows in schematic fashion an absorption chiller into which an apparatus $V_2$ is integrated.

FIGS. 1 and 2 elucidated hereinbelow show preferred embodiments of the process according to the invention and of the apparatus according to the invention.

FIG. 1 (abbreviated to "FIG. 1") shows an embodiment of the apparatus $V_2/V_1$ according to the invention.

The apparatus $V_1$ shown in FIG. 1 comprises a water absorption unit $W_{abs1}$ <103> (with optional additional heat exchanger $W_{z1}$ <104>) to which a conduit <101> leads and from which a conduit <102> leads away, a water desorption unit $W_{des1}$ which comprises a heat exchanger $W_{x1}$ <108> and a water desorber <109> and to which conduit <111> leads and from which conduits <110>, <112> and <113> lead away, and a circuit $U_2$ formed from conduits <106>, <111> and <113> or <106>, <111>, <112> and <105> (in each case optionally with conduit <114>). The apparatus in FIG. 1 may also optionally comprise a further heat exchanger $W_{y1}$ <107> to which conduits <106> and <112> lead and from which conduits <105> and <111> lead away. In addition the apparatus $V_1$ also comprises a liquid absorption medium $A_1$. Said medium is located in one or more of the abovementioned components water absorption unit $W_{abs1}$, water desorption unit $W_{des1}$, circuit $U_1$. The water absorption unit $W_{abs1}$ <103> may optionally also comprise an additional heat exchanger $W_{z1}$ <104> with which the liquid absorption medium $A_1$ may be brought, for example, to a temperature of 10° C. to 100° C., preferably 15° C. to 80° C., more preferably 20° C. to 50° C., yet more preferably 20° C. to 30° C. Optionally, circuit $U_2$ may also additionally comprise a pump for conveying the liquid absorption medium $A_1$.

The process according to the invention will now be illustratively described with reference to apparatus $V_1$ using FIG. 1:

A stream of moist gas mixture $G_1$ having, for example, a temperature of 2° C. to 100° C. (said stream may be moist air, moist natural gas or moist gas mixture—see also FIG. 2 with regard to this option) is supplied via conduit <101> to a water absorption unit $W_{abs1}$ <103> and contacted there with the liquid absorption medium $A_1$ supplied to the water absorption unit $W_{abs1}$ <103> via the conduit <105> or via the conduit <113>. The water absorption unit $W_{abs1}$ <103> may be any of the water absorbers recited hereinabove for $W_{abs1}$, in particular a falling-film. Contacting, in the water absorption unit $W_{abs1}$ <103>, the gas mixture $G_1$ supplied via conduit <101> with the liquid absorption medium $A_1$ supplied via the conduit <105> or via the conduit <113> affords a liquid absorption medium $A_2$ having an elevated water content compared to the liquid absorption medium $A_1$ and a stream of a gas mixture $G_2$ discharged via the conduit <102>, wherein $G_2$ has a lower water content compared to the moist gas mixture $G_1$. Depending on the application, $G_2$ is in particular dehumidified natural gas. The water absorption unit $W_{abs1}$ <103> may optionally also comprise an additional heat exchanger $W_{z1}$ <104> with which the liquid absorption medium $A_1$ may be adjusted, for example, to a temperature in the range of 10° C. to 100° C., preferably 15° C. to 80° C., more preferably 20° C. to 50° C., yet more preferably 20° C. to 30° C. Preferably via the conduits <106>, <111> and the heat exchanger $W_{y1}$ <107> (or, when the heat exchanger $W_{y1}$ <107> is not employed, via conduits <106>, <111> and <114>) the liquid absorption medium $A_2$ is then passed to the water desorption unit $W_{des1}$ composed of the heat exchanger $W_{x1}$ <108> and the water desorber <109>. The water-laden liquid absorption medium $A_2$ may additionally be supplied with heat in the optional heat exchanger $W_{y1}$ <107>. The at least partial removal of water from the liquid absorption medium $A_2$ is then carried out in the water desorber <109> to afford a liquid absorption medium $A_3$ having a lower water content compared to the liquid absorption medium $A_2$. The water removed is then discharged from the water desorber <109> as liquid or vapour, preferably as vapour, via a conduit <110>. The liquid absorption medium $A_3$ is then discharged from the water desorber <109> and returned to the water absorption unit <103>. This may Wand either be carried out directly, i.e. via the conduit <113> which is shown in dashed form in FIG. 1. Alternatively and preferably, the liquid absorption medium $A_3$ may also be supplied via the conduit <112> to the optional heat exchanger $W_{y1}$ <107> in which the liquid absorption medium $A_2$ supplied via conduit <106> to the optional heat exchanger $W_{y1}$ <107> is then supplied with heat from the liquid absorption medium $A_3$ supplied via conduit <112> to the optional heat exchanger $W_{y1}$ <107>. Once the concentrated liquid absorption medium $A_3$ has been supplied to the water absorption unit $W_{abs1}$ via conduit <105> or <113>, said medium is reused as $A_1$ for at least partially dehumidifying the gas stream in a new cycle.

FIG. 2 (abbreviated as "FIG. 2") shows in schematic fashion an absorption chiller into which an apparatus $V_2$ is integrated. The constituents <101> to <114> are shown as for the apparatus $V_2$ described in FIG. 1. Additionally, the absorption chiller in FIG. 2 also comprises a condenser <211> which is connected to the water desorption unit $W_{des2}$ <109> via the conduit <110> and is set up for condensing water at least partially removed from the liquid absorption medium $A_{1*}$ in the water desorption unit $W_{des2}$. The condenser <211> preferably also comprises a heat exchanger <212> with which cooling water may be supplied.

The absorption chiller shown in FIG. 2 also comprises an evaporator <214> connected to the condenser <211> via a conduit <216> (which may optionally comprise a throttling means <213>) and connected via the conduit <101> with the water absorption unit $W_{abs2}$. The evaporator <214> is set up to evaporate condensed water from the condenser. Additionally, the evaporator <214> can further preferably also comprise a heat exchanger <215> which supplies a medium, heat being drawn off from the medium to thus evaporate the condensed water (for example a coolant conduit with, in particular, water as coolant, this coolant being passed into the evaporator <214>). In an embodiment of the process according to the invention (described hereinbelow with reference to apparatus $V_1$ using FIG. 2) moist gas mixture G originating from the evaporator <214> is passed via the conduit <101> to the water absorption unit $W_{abs1}$ <103>. The water removed in water desorption unit $W_{des1}$ is supplied via the conduit <110> to the condenser <211> in which said water is recondensed. A cooling water circuit as heat exchanger <212> installed in the condenser is optionally likewise used therefor. The condensed water is then supplied via a conduit <216> to the evaporator <214> in which the evaporation of water is effected in particular at low pressures, thus bringing about a cooling effect. This may optionally also be effected using a throttling means <213>. This achieves a cooling action in the evaporator <214> and, for example, coolant may be cooled via the heat exchanger <215>. The water vapour generated is then returned to the water absorption unit $W_{abs1}$ <103> via conduit <101>.

The examples which follow are intended to elucidate the present invention without limiting said invention in any way.

EXAMPLES

In order to simulate the decomposition, 0.1 g of the following mixtures of 1-ethyl-3-methylimidazolium diethyl phosphate ("EMIM DEP", prepared according to WO 2004/016631 A1) and triethyl phosphate ("TEP"; purchased from Sigma Aldrich; CAS number: 78-40-0) were incubated at 150° C. for 20 minutes.

C1: Mixture of 85% by weight EMIM DEP and 15% by weight $H_2O$;
I1: Mixture of 75% by weight EMIM DEP, 15% by weight $H_2O$, 10% by weight TEP;
I2: Mixture of 80% by weight EMIM DEP, 15% by weight $H_2O$, 5% by weight TEP;
I3: Mixture of 84% by weight EMIM DEP, 15% by weight $H_2O$, 1% by weight TEP.

After the incubation, the gas phase was investigated by gas chromatography and mass spectrometry for the decomposition product N-methylimidazole.

The areas of the intensity peaks of the N-methylimidazole peak, measured using a flame ionization detector, are directly proportional to the proportion in the gas phase.

Whereas in the sample C1 a distinct N-methylimidazole peak was observed, this peak is absent in the samples I1, I2, I3. This shows the surprisingly stabilizing effect of triethyl phosphate.

Corresponding results are also observed for other trialkyl phosphates.

All references cited herein are fully incorporated by reference. Having now fully described the invention, it will be understood by those of skill in the art that the invention may be practiced within a wide and equivalent range of conditions, parameters and the like, without affecting the spirit or scope of the invention.

What is claimed is:

1. A process for dehumidifying a moist gas mixture $G_1$, wherein the moist gas mixture $G_1$ is contacted with a liquid absorption medium $A_1$, which comprises a mixture of at least one trialkyl phosphate of structure (I):

and at least one salt S selected from the group consisting of $Q^+A^-$, $Q^+(R^1O)_2PO_2^-$, $(Q^+)_2R^2OPO_3^{2-}$, and $Q^+M^+R^3OPO_3^{2-}$, to obtain a gas mixture $G_2$ which has a lower water content compared to the moist gas mixture $G_1$ and a liquid absorption medium $A_2$ which has an elevated water content compared to the liquid absorption medium $A_1$; wherein:
a) $Q^+$ is a dialkylimidazolium cation;
b) $A^-$ is an anion selected from the group consisting of $R^*COO^-$, $R'SO_3^-$, $HSO_4^-$, and $R''SO_4^-$;
c) $R^*$, $R'$, $R''$, $R^A$, $R^B$, $R^C$ are each independently an alkyl group;
d) $R^1$, $R^2$, $R^3$ are each independently an alkyl group; and
e) $M^+$ is an alkali metal ion.

2. The process of claim 1, wherein:
a) $Q^+$ is a dialkylimidazolium cation, in which the alkyl groups each independently have 1 to 10 carbon atoms;
b) $R^*$, $R'$, $R''$, $R^A$, $R^B$, $R^C$, $R^1$, $R^2$, $R^3$ are each independently an alkyl group having 1 to 10 carbon atoms; and
c) $M^+ = Li^+$, $K^+$ or $Na^+$.

3. The process of claim 1, wherein:
a) salt S is selected from the group of: $Q^+A^-$, and $Q^+(R^1O)_2PO_2^-$;
b) $Q^+$ is a dialkylimidazolium cation, in which the alkyl groups each independently have 1 to 6 carbon atoms;
c) $A^-$ is an anion selected from the group consisting of $R^*COO^-$, $R'SO_3^-$, and $R''SO_4^-$; and
d) $R^*$, $R^1$, $R'$, $R''$, $R^A$, $R^B$, and $R^C$ are each independently an alkyl group having 1 to 6 carbon atoms.

4. The process of claim 1, wherein $R^A$, $R^B$, and $R^C$ are each independently either methyl or ethyl.

5. The process of claim 1, wherein the liquid absorption medium $A_1$ is an aqueous solution.

6. The process of claim 5, wherein, in the liquid absorption medium $A_1$:
a) the total weight of all trialkyl phosphates of structure (I) and all salts S is in the range of 65% by weight to 95% by weight, based on the total weight of the aqueous solution; or
b) the ratio of the total weight of all trialkyl phosphates of structure (I) to the total weight of all salts S is in the range from 1:9999 to 1:9.

7. An apparatus $V_2$ for dehumidifying a moist gas mixture, comprising the components:
(i) a liquid absorption medium $A_{1*}$, which comprises a mixture of at least one trialkyl phosphate of structure (I):

and at least one salt S selected from the group consisting of $Q^+A^-$, $Q^+(R^1O)_2PO_2^-$, $(Q^+)_2R^2OPO_3^{2-}$, and $Q^+M^+R^3OPO_3^{2-}$;
(ii) at least one water absorption unit $W_{abs2}$ set up for contacting the moist gas mixture with the liquid absorption medium $A_{1*}$;
(iii) at least one water desorption unit $W_{des2}$ which comprises a heat exchanger $W_{x2}$ and is set up for at least partially removing water from a liquid absorption medium $A_{1*}$;

(iv) and a circuit $U_2$ which connects the water absorption unit $W_{abs2}$ with the water desorption unit $W_{des2}$ and by means of which the liquid absorption medium $A_{1*}$ may be circulated;

wherein:

$Q^+$ is a dialkylimidazolium cation;

$A^-$ is an anion selected from the group consisting of $R^*COO^-$, $R'SO_3^-$, $HSO_4^-$, and $R''SO_4^-$;

$R^*$, $R'$, $R''$, $R^A$, $R^B$, and $R^C$ are each independently an alkyl group;

$R^1$, $R^2$, and $R^3$ are each independently an alkyl group; and $M^+$ is an alkali metal ion.

8. The apparatus $V_2$ of claim 7, wherein in $A_{1*}$:
a) $Q^+$ is a dialkylimidazolium cation, in which the alkyl groups each independently have 1 to 10 carbon atoms;
b) $R^*$, $R'$, $R''$, $R^A$, $R^B$, $R^C$, $R^1$, $R^2$, $R^3$ are each independently an alkyl group having 1 to 10 carbon atoms; and
c) $M^+=Li^+$, $K^+$ or $Na^+$.

9. The apparatus $V_2$ of claim 7, wherein in $A_{1*}$:
a) salt S is selected from the group consisting of: $Q^+A^-$ and $Q^+(R^1O)_2PO_2^-$;
b) $Q^+$ is a dialkylimidazolium cation, in which the alkyl groups each independently have 1 to 6 carbon atoms;
c) $A^-$ is an anion selected from the group consisting of: $R^*COO^-$, $R'SO_3^-$, and $R''SO_4^-$; and
d) $R^*$, $R^1$, $R'$, $R''$, $R^A$, $R^B$, and $R^C$ are each independently an alkyl group having 1 to 6 carbon atoms.

10. The apparatus $V_2$ of claim 7, wherein $R^A$, $R^B$, $R^C$ are mutually independently either methyl or ethyl.

11. The apparatus $V_2$ of claim 7, wherein the liquid absorption medium $A_{1*}$ is an aqueous solution.

12. The apparatus $V_2$ of claim 11, wherein in $A_{1*}$:
a) the total weight of all trialkyl phosphates of structure (I) and all salts S is in the range of 65% by weight to 95% by weight, based on the total weight of the aqueous solution; or
b) the ratio of the total weight of all trialkyl phosphates of structure (I) to the total weight of all salts S is in the range from 1:9999 to 1:9.

13. The apparatus $V_2$ of claim 7, wherein $V_2$ is part of an absorption heat pump, that further comprises a condenser; an evaporator; and a coolant, wherein the coolant is water.

14. An absorption medium $A_{1*}$, comprising a mixture of at least one trialkyl phosphate of structure (I):

and at least one salt S selected from the group consisting of: $Q^+A^-$, $Q^+(R^1O)_2PO_2^-$, $(Q^+)_2R^2OPO_3^{2-}$, and $Q^+M^+ R^3OPO_3^{2-}$; wherein:
a) $Q^+$ is a dialkylimidazolium cation;
b) $A^-$ is an anion selected from the group consisting of $R^*COO^-$, $R'SO_3^-$, $HSO_4^-$, and $R''SO_4^-$;
c) $R^*$, $R'$, $R''$, $R^A$, $R^B$, $R^C$, $R^1$, $R^2$, and $R^3$ are each independently an alkyl group; and
d) $M^+$ is an alkali metal ion.

15. The absorption medium $A_{1*}$ of claim 14, wherein:
a) $Q^+$ is a dialkylimidazolium cation, in which the alkyl groups each independently have 1 to 10 carbon atoms;
b) $R^*$, $R'$, $R''$, $R^A$, $R^B$, $R^C$, $R^1$, $R^2$, and $R^3$ are each independently an alkyl group having 1 to 10 carbon atoms; and
c) $M^+=Li^+$, $K^+$ or $Na^+$.

16. The absorption medium $A_{1*}$ of claim 14, wherein:
a) salt S is selected from the group consisting of: $Q^+A^-$ and $Q^+(R^1O)_2PO_2^-$;
b) $Q^+$ is a dialkylimidazolium cation in which the alkyl groups each independently have 1 to 6 carbon atoms;
c) $A^-$ is an anion selected from the group consisting of: $R^*COO^-$, $R'SO_3^-$, and $R''SO_4^-$; and
d) $R^*$, $R^1$, $R'$, $R''$, $R^A$, $R^B$, and $R^C$ are each independently an alkyl group having 1 to 6 carbon atoms.

17. The absorption medium $A_{1*}$ of claim 14, wherein $R^A$, $R^B$, $R^C$ are mutually independently either methyl or ethyl.

18. The absorption medium $A_{1*}$ of claim 14, wherein is $A_{1*}$ is an aqueous solution.

19. The absorption medium $A_{1*}$ of claim 14, in which the total weight of all trialkyl phosphates of structure (I) and all salts S is in the range of 65% by weight to 95% by weight, based on the total weight of the aqueous solution.

20. The absorption medium $A_{1*}$ of claim 14, in which the ratio of the total weight of all trialkyl phosphates of structure (I) to the total weight of all salts S is in the range from 1:9999 to 1:9.

* * * * *